United States Patent [19]

Godfrey et al.

[11] 4,180,564
[45] Dec. 25, 1979

[54] A-38533 ANTIBIOTICS AND PROCESS FOR PRODUCTION THEREOF

[75] Inventors: Otis W. Godfrey, Greenwood; Ronald D. Johnson; Ralph E. Kastner, both of Indianapolis, all of Ind.

[73] Assignee: Eli Lilly and Company, Indianapolis, Ind.

[21] Appl. No.: 909,582

[22] Filed: May 25, 1978

[51] Int. Cl.$^2$ .............................................. A61K 35/00
[52] U.S. Cl. .................................. 424/117; 424/115; 424/118; 435/68; 435/886
[58] Field of Search ....................... 424/115, 117, 118; 195/80 R

[56] References Cited
PUBLICATIONS

Chemical Abstracts 85: 121791(x), (1976).

*Primary Examiner*—Jerome D. Goldberg
*Attorney, Agent, or Firm*—Nancy J. Harrison; Arthur R. Whale

[57] ABSTRACT

Antibiotic A-38533 complex, comprising microbiologically active, related factors $A_1$, $A_2$, B and C, is produced by submerged, aerobic fermentation of a new *Streptomyces sp.*, NRRL 11298. The A-38533 antibiotics are closely related antibiotics. The individual A-38533 factors are separated by chromatography. The A-38533 factors are antibacterial agents which have a unique activity against *Pseudomonas* species.

11 Claims, 4 Drawing Figures

A-38533 ANTIBIOTICS AND PROCESS FOR PRODUCTION THEREOF

BACKGROUND OF THE INVENTION

1. Field of the Invention

This invention relates to a group of antibiotics which have a unique activity against Pseudomonas species. Pseudomonas species have been implicated in a variety of serious infections, such as meningitis, respiratory infections, urinary tract infections, intestinal infections (infants), joint infections and otitis. *P. aeruginosa* causes a dangerous infection of the eye. Pseudomonas species are common infectious agents in aerobic wound infections. *P. aeruginosa* is one of the three organisms which are most likely to infect burns. Neonatal meningitis caused by Pseudomonas is associated with a high mortality rate and a high incidence of residual neurological damage. Agents which are active against Pseudomonas are, therefore, greatly needed. Pseudomonas species are generally refractive to most antibiotics.

2. The Prior Art

The A-38533 antibiotics belong to a new class of antibiotics and appear to be related to antibiotic 6798 RP (British Patent No. 846,801) and to the recently discovered antibiotic FR 3383 [see unexamined Japanese patent applications 1054-988 (Derwent Abstract No. 49101X) and 2092-881 (Derwent Abstract No. 66033Y); Japanese Kokai 76 54,988 (Chem. Abstr. 85: 121791x); and presentation of K. Umehara et al. at the 207th Scientific Meeting JNRA, November, 1977, "Studies on a new antibiotic FR 3383. Discovery, fermentation, extraction, chemical and biological properties." (Fujisawa Yakuhin Central Res. Labs.)]. Antibiotic FR 3383 differs from A-38533 factors $A_1$, B and C in movement in chromatographic systems and differs from A-38533 factor $A_2$ in that FR 3383 contains 3.3% sulfur (see Derwent Abstract No. 66033Y) whereas A-38533 factor $A_2$ contains only trace amounts of sulfur by elemental analysis.

SUMMARY OF THE INVENTION

This invention relates to antibiotic substances. In particular, it relates to an antibiotic complex comprising several factors, including individual factors $A_1$, $A_2$, B and C. This complex is produced by culturing a hitherto undescribed Streptomyces species NRRL 11298.

The term "complex" as used in the fermentation art and in this specification refers to a mixture of coproduced individual antibiotic factors. As will be recognized by those familiar with antibiotic production by fermentation, the number and ratio of individual factors produced in an antibiotic complex will vary, depending upon the fermentation conditions and strain used.

The antibiotic substances of this invention are arbitrarily designated herein as A-38533 antibiotics. The A-38533 complex contains several individual factors which are designated A-38533 factors $A_1$, $A_2$, B and C. In discussions of utility, the term "A-38533 antibiotic" will be used, for the sake of brevity, to denote a member selected from the group consisting of A-38533 complex, A-38533 factors $A_1$, $A_2$, B and C and the pharmaceutically-acceptable salts thereof.

The A-38533 complex is produced by culturing Streptomyces sp. NRRL 11298 under submerged aerobic fermentation conditions until a substantial level of antibiotic activity is produced. The A-38533 complex is most readily separated from the filtered fermentation broth by adsorption onto a resin column, elution of the column with an aqueous alcohol solution, and evaporation of the eluate to obtain the A-38533 complex. The A-38533 complex can be further purified and separated into its individual factors by chromatographic techniques. The A-38533 antibiotics of this invention inhibit the growth of certain pathogenic microorganisms, in particular those within the genus Pseudomonas.

DESCRIPTION OF THE DRAWINGS

Infrared absorption spectra (in KBr pellet) of A-38533 factors $A_1$, $A_2$, B and C are presented in the drawings as follows.

DETAILED DESCRIPTION

Figure 1:
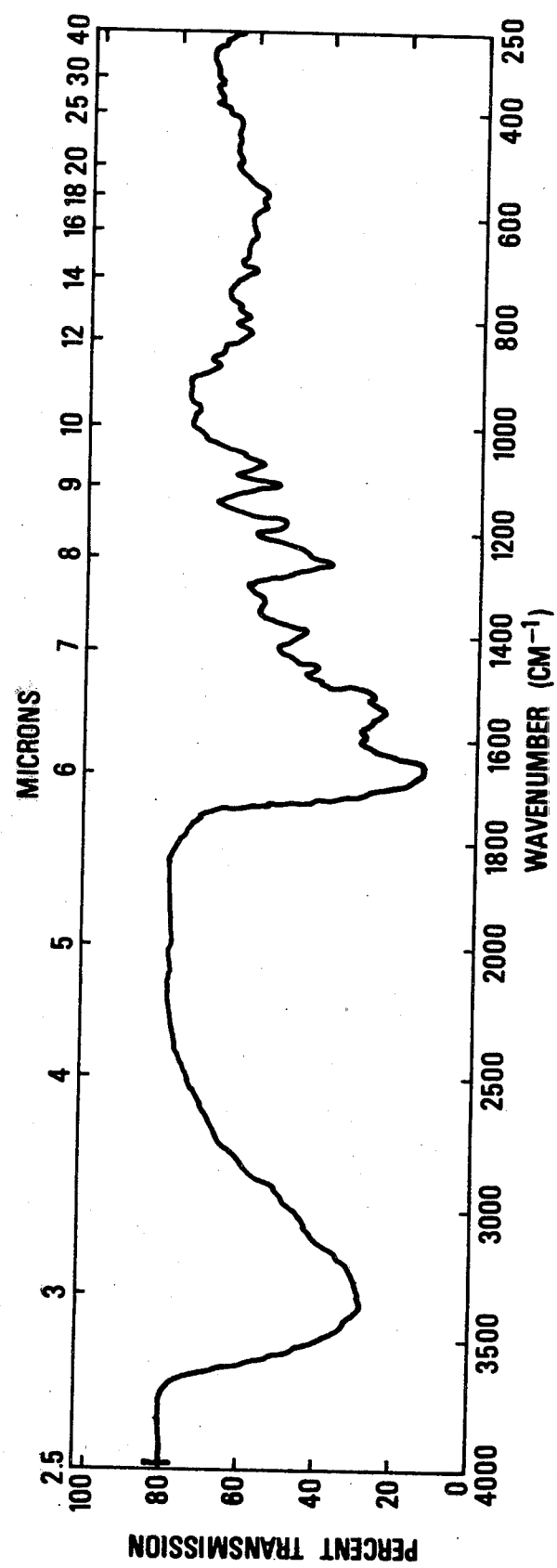
FIG. 1—A-38533 factor $A_1$
FIG. 2—A-38533 factor $A_2$
FIG. 3—A-38533 factor B
FIG. 4—A-38533 factor C

The A-38533 factors of this invention are closely related compounds. As many as four antibiotic factors are recovered from the fermentation and are obtained as a mixture, the A-38533 complex. It will be recognized that the ratio of the factors in the A-38533 complex will vary, depending upon the fermentation conditions used. In general, however, A-38533 factor B is the major component of the complex, accounting for approximately 60 percent of the complex. A-38533 factor $A_1$ is present in amounts of approximately 25 percent. A-38533 factors $A_2$ and C are minor factors, together accounting for approximately 15 percent of the A-38533 complex. The individual factors $A_1$, $A_2$, B and C are separated and isolated as individual compounds as hereinafter described. The A-38533 complex is soluble in water, methanol, dimethyl sulfoxide, dimethylformamide, and alcohol-water and tetrahydrofuran-water mixtures.

The characteristics of the individual A-38533 factors of this invention are summarized in the following tables. The A-38533 factors $A_1$, $A_2$, B and C are isolated as noncrystalline white powders. The approximate percentage elemental compositions of the A-38533 factors are shown in Table I.

Table I

| | Elemental Analyses of A-38533 Factors | | | | | |
|---|---|---|---|---|---|---|
| Factor | % Carbon | % Hydrogen | % Nitrogen | % Oxygen | % Sulfur | % Ash |
| $A_1$ | 53.3–54.9 | 5.5–5.7 | 12.4–12.7 | 24.3–25.6 | 3.3–3.8 | 0 |
| $A_2$ | 54.0–55.0 | 5.0–6.0 | 12.5–13.5 | 24.0–25.0 | trace | 0 |
| B | 54.4–55.1 | 5.3–5.6 | 13.4–13.9 | 22.1–22.9 | 3.3–3.6 | 0 |
| C | 54.5–54.7 | 5.1–5.7 | 13.8–14.1 | 22.2–23.9 | trace | 0 |

The ultraviolet and visible absorption spectra of the A-38533 factors exhibit maxima which are summarized in Table II.

Table II

| | UV and Visible Spectrophotometry of A-38533 Factors | |
|---|---|---|
| Factor | Acidic or Neutral $\lambda_{max}$nm ($\epsilon$) | Basic $\lambda_{max}$nm ($\epsilon$) |
| $A_1$ | 256 (21,500) 222 (28,500) | 290 (7500); 260 (s) (22,400); 242 (35,500) |
| $A_2$ | 256 (20,500) 222 (26,500) | 290 (6400); 260 (s) (21,600); 242 (32,000) |
| B | 290 (6150); 258 (22,600); 222 (48,000) | 290 (8600); 260 (s) (23,000); 243 (25,000); 222 (s) (53,800) |
| C | 290 (6000); 259 (21,000); | 290 (8500); 260 (s) (21,600); |

Table II-continued

| | UV and Visible Spectrophotometry of A-38533 Factors | |
|---|---|---|
| Factor | Acidic or Neutral $\lambda_{max}$nm ($\epsilon$) | Basic $\lambda_{max}$nm ($\epsilon$) |
| | 222 (46,000) | 243 (25,400); 222 (s) (51,700) |

The approximate molecular weights of the A-38533 factors, as determined by plasma-desorption mass spectrometry and field-desorption mass spectrometry, are summarized in Table III.

Table III

| | Molecular Weights of A-38533 Factors | | |
|---|---|---|---|
| | Mass Spectrometry | | |
| Factor | Plasma Desoprtion | Field Desorption | Confirmed by Acetyl Derivative |
| A$_1$ | 840 | 840 | 840 |
| A$_2$ | 822 | 822 | — |
| B | 863 | 863 | 863 |
| C | not done | 846 | — |

Table IV summarizes the titratable groups which were determined by electrometric titration of the A-38533 factors in 66% aqueous dimethylformamide.

Table IV

| | Titration of A-38533 Factors | | | | |
|---|---|---|---|---|---|
| pK | Factor A$_1$ | Factor A$_2$ | Factor B | Factor C | Tentative Assignments |
| pK$_1$ | 5.93–6.02 | 6.10 | 6.20 | 6.20 | carboxyl |
| pK$_2$ | 7.71–7.88 | 7.84 | 7.84 | 7.86 | amino |
| pK$_3$ | 10.80–10.90 | 10.80 | 10.80 | 10.81 | uracil |
| pK$_4$ | 12.0–12.6 | >12.0 | 12.75 | 13.0 | phenolic |
| pK$_5$ | >13.0 | >13.0 | — | — | phenolic |

On the basis of a series of potentiometric, UV, and circular dichroism (CD) studies on A-38533 factors A$_1$, A$_2$ and B, it is postulated that the following groups may be present in each of these factors:

(1) α-COOH of peptide moiety;
(2) α-NH$_2$ of peptide moiety;
(3) uracil moiety;
(4) tyrosine moiety.

Hydrolysis of A-38533 factor B with 6 N hydrochloric acid at boiling temperature for 21 hours and subsequent chromatographic (BioRex 70) separation led to the isolation and characterization of the following compounds:

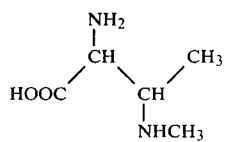

2-amino-3-(methylamino)butyric acid

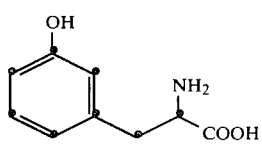

m-tyrosine

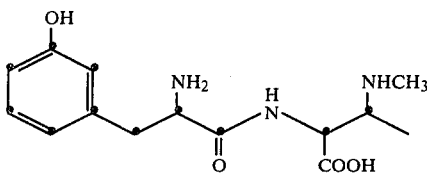

dipeptide of the above two compounds

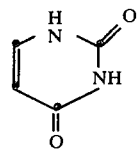

uracil

Based upon the amounts isolated from the hydrolysis reaction, A-38533 factor B contains one residue each of 2-amino-3-(methylamino)butyric acid, m-tyrosine, and uracil.

The molecular formulas for A-38533 factors A$_1$ and B are $C_{37}H_{44}N_8O_{13}S$ and $C_{39}H_{45}N_9O_{12}S$, respectively.

Chemical studies have established that uracil is also a component of A-38533 factors A$_1$ and C.

The A-38533 factors contain hydroxyl and/or amino groups which are capable of acylation by standard procedures. When A-38533 factor B is peracetylated using acetic anhydride and pyridine, for example, a tetraacetate derivative is obtained. When A-38533 factor A$_1$ is similarly peracetylated, a pentaacetate derivative is obtained.

Figure 2:
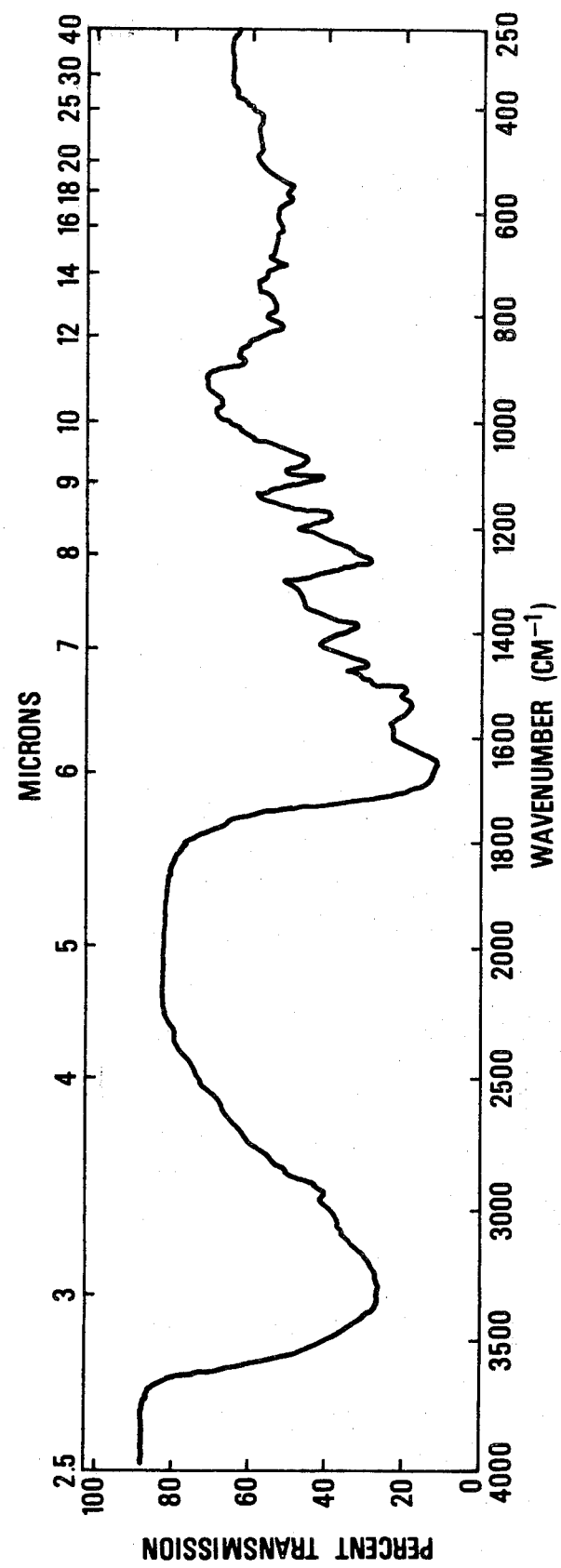
Figure 3:
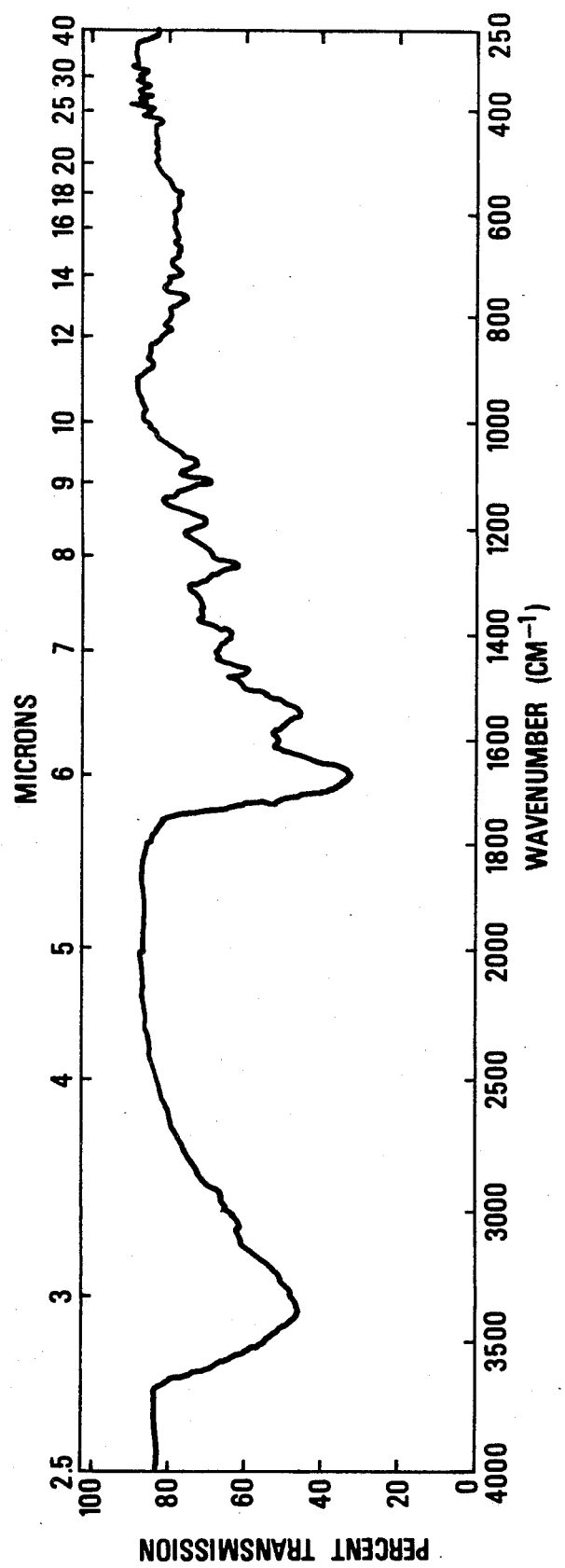
Figure 4:
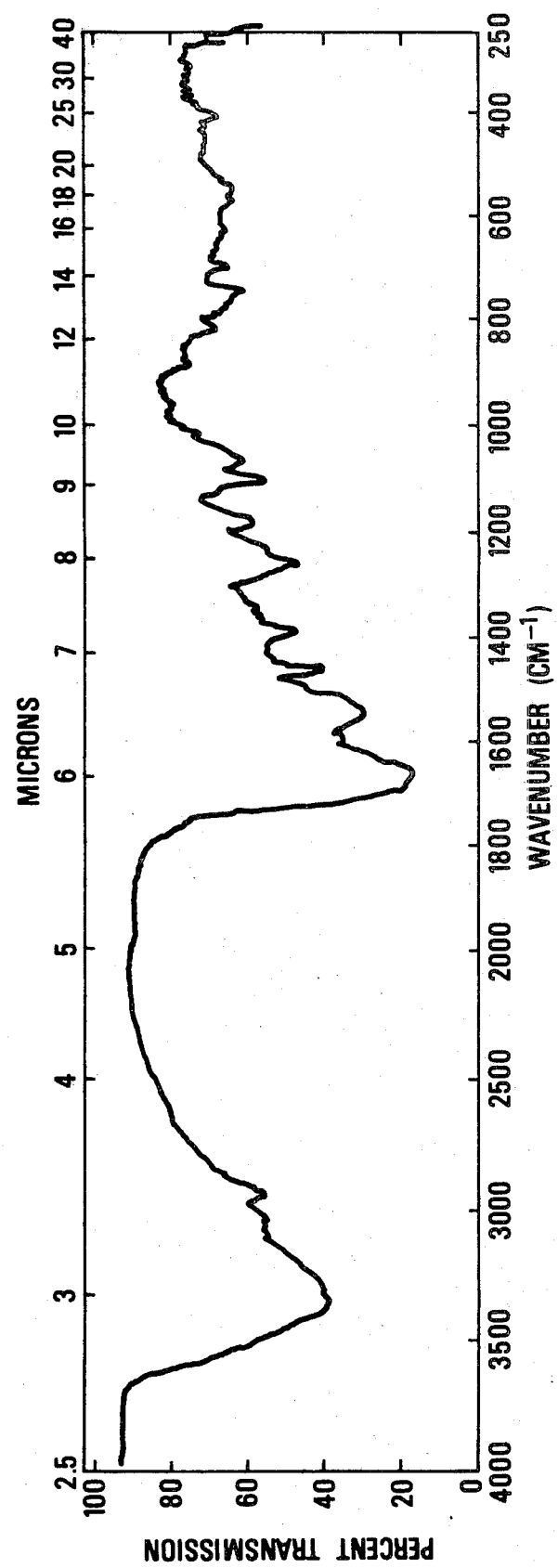

The infrared absorption spectra of A-38533 factors A$_1$, A$_2$, B and C in KBr pellet are shown in FIGS. 1–4, respectively, of the accompanying drawings. Table V summarizes the most significant absorption maxima observed in these spectra.

Table V

| IR Maxima (cm$^{-1}$) of the A-38533 Factors | | | |
|---|---|---|---|
| A$_1$ | A$_2$ | B | C |
| 3363 | 3350 | 3363 | 3362 |
| 1665 | 2940 | 1663 | 3040 |
| 1593 | 1656 | 1593 | 2950 |
| 1552 | 1535 | 1550 | 1660 |
| 1518 | 1505 | 1463 | 1540 |
| 1465 | 1458 | 1397 | 1455 |
| 1396 | 1383 | 1362 | 1385 |
| 1363 | 1255 | 1268 | 1260 |
| 1268 | 1170 | 1183 | 1175 |
| 1185 | 1100 | 1110 | 1098 |
| 1112 | 1062 | 1072 | 1063 |
| 1073 | 955 | 965 | 955 |
| 964 | 880 | 890 | 875 |
| 887 | 810 | 820 | 810 |
| 822 | 755 | 755 | 745 |
| 792 | 695 | 708 | 695 |
| 708 | 625 | 635 | 570 |
| 635 | 568 | 580 | 540 |
| 582 | 543 | 555 | 410 |
| 555 | 475 | — | — |
| 490 | 410 | — | — |

The color reactions of three of the A-38533 factors are summarized in Table VI. Table VI also includes for comparison the known color reactions of the two prior art antibiotics which are believed to be most closely related to the A-38533 antibiotics.

Table VI

| Reaction | Indication | A38533-A$_1$ | A38533-B | A38533-C | 6798RP* | FR3383* |
|---|---|---|---|---|---|---|
| Biuret | peptide | — | — | — | — | + |
| Folin | phenolic OH | — | — | — | + | + |
| Anthrone | ketoses | — | — | — | — | — |
| Dragendorff | tert-amines | — | — | — | — | — |
| Molish | sugars | + | + | + | + | — |
| Ehrlich | indoles | — | + | + | — | — |
| Sakaguchi | guanidine | — | — | — | — | — |
| Ninhydrin | amino acid or amines | — | — | — | — | |
| FeCl$_3$ | phenolic or enolic OH | — | — | — | — | |
| Pauly | amines and phenols | + | + | + | | |

*data from literature

The A-38533 factors are soluble in water. The solubility in water, however, decreases from factor A$_1$ (most soluble to factor C (least soluble). The A-38533 factors are also soluble in methanol; the solubility in methanol increases from factor A$_1$ (least soluble) to factor C (most soluble). The A-38533 factors are more soluble in methanol on the acidic side and in water on the basic side. The A-38533 factors are also soluble in dimethyl sulfoxide, dimethylformamide and in alcohol-water and tetrahydrofuran-water mixtures.

The A-38533 factors are stable at various pH levels. For example, Table VII summarizes the stability of factor A$_1$ when tested in water at pH levels of 2, 4, 7, 9 and 11 both at 5° C. and at room temperature over a 16-day period. The assay organism was *Pseudomonas aeruginosa*.

Table VII
Stability Study of A-38533 Factor A$_1$
*P. aeruginosa* Assay in units/mg

| pH | Temp. | Day 0 | Day 1 | Day 3 | Day 8 | Day 13 | Day 16 |
|---|---|---|---|---|---|---|---|
| 2 | 5° C. | 250 | 250 | 230 | 225 | 230 | 228 |
|  | RT* | 285 | 250 | 185 | 210 | 190 | 185 |
| 4 | 5° C. | 230 | 240 | 215 | 230 | 205 | 252 |
|  | RT | 225 | 220 | 205 | 235 | 225 | 237 |
| 7 | 5° C. | 245 | 270 | 215 | 250 | 240 | 235 |
|  | RT | 220 | 280 | 230 | 250 | 240 | 257 |
| 9 | 5° C. | 235 | 250 | 220 | 245 | 215 | 230 |
|  | RT | 230 | 210 | 220 | 215 | 200 | 210 |
| 11 | 5° C. | 250 | 220 | 205 | 195 | 180 | 205 |
|  | RT | 250 | 240 | 190 | 198 | 190 | 195 |

*RT = room temperature

The A-38533 factors A$_1$, A$_2$, B and C are most conveniently separated and identified by high-performance liquid chromatography (HPLC) and by thin-layer chromatography (TLC).

The preferred TLC system for separating the A-38533 factors uses reverse-phase C$_{18}$ silylated silica-gel TLC plates [Quantum Industries, 5-×20-cm, precoated C$_{18}$ Nano/gram plates with fluorescent indicator (254 nm), 10μ thick on glass], eluting with a 0.5 M citrate buffer (pH 4):methanol (1:1) solvent system. Table VIII gives the approximate R$_f$ values for the A-38533 factors in this system:

Table VIII

| A-38533 Factor | R$_f$ Value |
|---|---|
| A$_1$ | 0.55 |
| A$_2$ | 0.49 |
| B | 0.38 |
| C | 0.33 |

Other solvent systems in which the A-38533 factors can be separated by reverse-phase TLC are methanol:1% aqueous ammonium carbonate (pH 8.5) solutions in ratios of either 7:3 or 3:2.

The preferred analytical separation of the A-38533 factors by HPLC uses the following conditions:

| | |
|---|---|
| Column Size: | 3/8" × 50 cm |
| Packing: | HP-1/C$_{18}$ laboratory-synthesized reverse-phase packing (10 μ) |
| Solvent: | 17% acetonitrile in 1% aqueous ammonium carbonate solution (pH 8.5) |
| Flow Rate: | 6 ml/min |
| Pressure: | 1000 psi |
| Detector: | variable wavelength UV at 260 nm |
| Sensitivity: | 0–0.04 A.U.F.S. |

Table IX gives the approximate retention times and volumes when 10 μg each of factors A$_1$ and A$_2$ and 15 μg each of factors B and C were injected.

Table IX

| A-38533 Factor | Retention Time (min) | Retention Volume (ml) |
|---|---|---|
| A$_1$ | 6.0 | 36.0 |
| A$_2$ | 8.2 | 49.2 |
| B | 16.5 | 99.0 |
| C | 28.3 | 169.8 |

As those skilled in the art will appreciate, because each of the A-38533 factors A$_1$, A$_2$, B and C contain a carboxyl and an amino moiety, they may exist in the form of salts. Such salts are useful for purification purposes. In addition, the pharmaceutically acceptable salts of the A-38533 factors are useful as antibacterial agents. "Pharmaceutically acceptable" salts refer to those salts in which the toxicity of the A-38533 factor as a whole toward warm-blooded animals in not increased relative to the non-salt form.

The acid addition salts of the A-38533 factors are formed by standard reaction with an inorganic or organic acid. Representative inorganic and organic acids include hydrochloric, hydrobromic, hydriodic, sulfuric, phosphoric, acetic, benzoic, sulfamic, tartaric, citric, maleic, succinic, ascorbic, glycolic, lactic, fumaric, palmitic, cholic, pamoic, mucic, D-glutamic, d-camphoric, glutaric, phthalic, lauric, stearic, salicyclic, methanesulfonic, benzenesulfonic, sorbic, picric, cinnamic, and other suitable acids.

The cationic salts of the A-38533 factors are prepared using standard procedures such as reacting the free acid with inorganic and organic bases and salts. Examples of these salts are ammonium and substituted ammonium salts; alkali-metal salts, such as sodium, potassium, lithium, cesium, and rubidium; and alkaline-earth metal salts such as calcium, strontium, and barium; copper, zinc, magnesium, and silver. In the instance of organic bases, the identity of the base is not critical, although, in general, a base having a pKa of 3.0 or above in water is preferred. Representative suitable organic bases include benzylamine, methylamine, diethylamine, triethylamine, procaine, diisopropylamine, ethanolamine, cyclohexylamine, dicyclohexylamine, diphenylamine, di-n-butylamine, quinoline, and pyridylamine.

Pharmaceutically acceptable salts are generally preferred for pharmaceutical applications. However, all salts are useful as intermediates in production, separation, and purification. For therapeutic purposes, pharmaceutically acceptable salts are generally equivalent to the free base or acid; however, particular salts are occasionally preferred due to a favorable property, such as solubility, conferred by the salt-forming moiety.

The novel antibiotics of this invention are produced by culturing an A-38533-producing species under submerged aerobic conditions in a suitable medium until optimal antibiotic activity is produced. The antibiotics are recovered by using various isolation and purification procedures understood in the fermentation art. The culture which is useful for the production of the A-38533 antibiotics initially was isolated from a soil sample, was subsequently biologically purified and now has been identified as belonging to the genus Streptomyces. This identification is based on the following characteristics:

(1) LL-diaminopimelic acid is present in the whole cell hydrolysate.
(2) The culture possesses aerial mycelia, and the sporophores are of the Rectus-Flexibilis (RF) type.
(3) Sporophores are present bearing catenulate spores >10 in number per chain.
(4) Spores, as observed by scanning electron microscopy, are cylindrical and smooth.
(5) Abundant growth was observed on several media (ISP #2, ISP #4, glucose-asparagine, tomato paste-oatmeal agar). Aerial mycelia were in the yellow color series, 2ba pale yellow. Substrate mycelia was light yellowish brown. No soluble pigments were observed.

These characteristics are common to, and characteristic of, the genus Streptomyces.

The Streptomyces sp. culture which is useful for the production of the A-38533 antibiotics has been deposited and made a part of the stock culture collection of the Northern Regional Research Center, U.S. Department of Agriculture, Agricultural Research Service, Peoria, Illinios, 61604, from which it is available to the public under the number NRRL 11298.

As is the case with other organisms, the characteristics of the A-38533-producing culture, Streptomyces sp. NRRL 11298, are subject to variation. For example, mutants (spontaneous or induced), transconjugants and recombinants (including recombinant DNA on plasmids) of the NRRL 11298 strain, or derived from this strain, which produce the A-38533 antibiotics may be used in this invention.

A number of different media may be used to produce the A-38533 complex with Streptomyces sp. NRRL 11298. For economy in production, optimal yield, and ease of product isolation, however, certain culture media are preferred. Thus, for example, preferred carbon sources for large-scale fermentation are glucose and tapioca dextrin, although glycerol and refined soybean oil also can be used. Optimum levels of carbon sources are from about 2 to about 5 percent.

Preferred nitrogen sources are soybean meal and casein, although soybean hydrolysate and fish meal can also be used.

Among the nutrient inorganic salts which can be incorporated in the culture media are the customary soluble salts capable of yielding sodium, magnesium, calcium, ammonium, chloride, carbonate, phosphate, sulfate, nitrate and like ions.

Essential trace elements necessary for the growth and development of the organism should also be included in the culture medium. These trace elements commonly occur as impurities in other constituents of the medium in amounts sufficient to meet the growth requirements of the organism.

It may be necessary to add small amounts (i.e., 0.2 ml/L.) of an antifoam agent such as polypropylene glycol to large-scale fermentation media if foaming becomes a problem.

For producing substantial quantities of the A-38533 antibiotics, submerged aerobic fermentation in tanks is preferred. However, small quantities of the A-38533 antibiotics may be obtained by shake-flask culture. For tank fermentation it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transfered to a larger tank where, after a short incubation time, the A-38533 complex is produced in optimal yield.

The A-38533-producing organism can be grown over a broad temperature range (about 20°-40° C.). Antibiotic production also occurs over a broad temperature range (about 25°-37° C.). Optimum A-38533 production appears to occur at temperatures of about 34° C.

As is customary in aerobic submerged culture processes, sterile air is dispersed through the culture medium. For efficient growth of the organism, the volume of air used in tank production is in the range from 0.25 to 0.5 volumes of air per volume of culture medium per minute (V/V/M) and from 200 to 400 RPM agitation. An optimum rate is about 0.35 V/V/M with agitation provided by a propeller rotating at 250 RPM in a 100-liter vessel, which provides a dissolved oxygen rate in water of 150 $\mu$M/min.

Production of the A-38533 antibiotics can be followed during fermentation by testing samples of the broth for antibiotic activity. An assay organism useful in testing these antibiotics is *Pseudomonas aeruginosa* ATCC 9027. The bioassay is preferably performed by paper-disc assay on agar plates.

Antibiotic activity is generally present after 24 hours and remains present for at least 6 days during the fermentation. Peak antibiotic production occurs at from about two to about three days fermentation time.

The A-38533 antibiotics can be recovered from the fermentation medium by methods used in the art. The A-38533 antibiotics generally are present in the broth. Maximum recovery of the A-38533 antibiotics is accomplished, therefore, by an initial filtration to remove the mycelial mass. The filtered broth can be purified to give the A-38533 complex by a variety of techniques. A preferred technique involves adsorption of the filtered broth on a macroreticular resin column and elution of the column with aqueous alcohol mixtures. The eluted fractions which exhibit antibiotic activity can be combined to give A-38533 complex. Alternatively, using this technique, the eluted fractions can be combined on the basis of factor content to give enriched mixtures of the various factors.

Further purification of the individual A-38533 factors includes additional adsorption and extraction procedures. Adsorptive materials such as florisil, silica gel, ion-exchange resins and the like can be advantageously used. High-performance liquid chromatography (HPLC) is an especially preferred tool for separating the A-38533 individual factors.

The A-38533 antibiotics inhibit the growth of certain gram-negative pathogenic organisms, particularly Pseudomonas species. The minimal inhibitory concentrations (MIC's) at which the A-38533 factors $A_1$, $A_2$, B and C inhibit various strains of *Pseudomonas aeruginosa* and *Neisseria gonorrhea*, as determined by standard agar-dilution tests, are summarized in Table X.

Table X

| | In Vitro A-38533 Activity | | | | | | | | | | | |
|---|---|---|---|---|---|---|---|---|---|---|---|---|
| | MIC (μg/ml) | | | | | | | | | | | |
| | *Pseudomonas aeruginosa* species | | | | | | | | | *Neisseria gonorrhea* species | | |
| Compound | X48 | X528 | X239 | PS9 | PS15 | PS25 | 4276 | PI23 | PA103 | Glov | Lind | Sand |
| Factor $A_1$ | 4 | 4 | 4 | 16 | 4 | 4 | 4 | 4 | 2 | 6.5 | 40 | 13.5 |
| Factor $A_2$ | 4 | 4 | 4 | 16 | 4 | 4 | 4 | 4 | 2 | NT* | NT | NT |
| Factor B | 4 | 8 | 4 | 32 | 8 | 8 | 8 | 4 | 4 | 19 | 45 | 24 |
| Factor C | 4 | 4 | 4 | 16 | 4 | 4 | 4 | 4 | 4 | NT | NT | NT |
| Carbencillin | 16 | 16 | 32 | 32 | 16 | 64 | 128 | 32 | 32 | NT | NT | NT |

*NT = not tested

The A-38533 antibiotics have shown in vivo antimicrobial activity against experimental bacterial infections. When three subcutaneous doses of an A-38533 factor were administered to mice with illustrative infections, the activity observed was measured as an $ED_{50}$ value [effective dose in mg/kg to protect 50% of the test animals; see Warren Wick, et al., *J. Bacteriol.* 81, 233–235 (1961)]. The $ED_{50}$ values which were observed for some of the A-38533 factors are summarized in Table XI. The $LD_{50}$ values in Table XI refer to the infecting challenge of the pathogen, the measure being the number by which the $LD_{50}$ (ip) of the infecting organism is multiplied.

Table XI

| In Vivo A-38533 Biological Testing *P. aeruginosa* Infection in Mice | | | | | | | |
|---|---|---|---|---|---|---|---|
| | | Test A *P. aeruginosa* X239 | | Test B *P. aeruginosa* 24J | | Test C *P. aeruginosa* 24J | |
| Compound | Route | $LD_{50}$ | $ED_{50}$ mg/kg | $LD_{50}$ | $ED_{50}$ mg/kg | $LD_{50}$ | $ED_{50}$ mg/kg |
| Factor $A_1$ | SC | 76 | 17.8×3 | 7.6 | 12.4×3 | 21.5 | 32.8×3 |
| Factor B | SC | 76 | 27.3×3 | 7.6 | 13.6×3 | 21.5 | 97×3 |
| Carbenicillin | SC | 76 | 29.3×3 | 7.6 | 31.9×3 | 21.5 | 57.5×3 |
| Tobramycin | SC | 76 | 0.4×2 | 7.6 | 0.4×2 | 21.5 | 0.6×2 |

Another advantage of the A-38533 antibiotics is that they are relatively nontoxic. For example, the $LD_{50}$ of the A-38533 complex and individual factors $A_1$ and B are shown in Table XII.

Table XII

| Acute Toxicity Testing in Mice | | |
|---|---|---|
| Factor | Route | $LD_{50}$, mg/kg × 1 |
| $A_1$ | IP | >2400 |
| B | IP | >2000 |
| Complex | IP | >300 |

In order to illustrate more fully the operation of this invention, the following examples are provided.

EXAMPLE 1

A. Shake-flask Fermentation of A-38533

A lyophilized pellet of Streptomyces sp. NRRL 11298 is dissolved in 1–2 ml of sterilized water. This solution is used to inoculate an agar slant having the following composition:

| Ingredient | Amount (Percent) |
|---|---|
| Dextrin | 1.0 |
| Yeast extract | 0.1 |
| Enzymatic hydrolysate of casein* | 0.2 |
| Beef extract | 0.1 |
| Agar | 2.0 |
| Deionized water | 96.6 |

*NZ Amine A, Humko-Sheffield Chemical, Lyndhurst, N.J.

The inoculated slant is incubated at 30° C. for from seven to ten days. The mature slant culture is covered with water (2 ml) and scraped with a sterile pipette to loosen the spores and mycelium. The resulting suspension is used to inoculate 50 ml of a vegetative medium having the following composition:

| Ingredient | Amount |
|---|---|
| Trypticase Soy Broth (Baltimore Biological Laboratories, Cockeysville, Md.) | 30 g/L. |
| Glycerol | 15 ml/L. |
| $CaCO_3$ | 2 g/L. |
| Tap water | q.s. 1 liter |

The inoculated vegetative medium is incubated in a 250-ml Erlenmeyer flask at 30° C. for about 48 hours on a shaker rotating through an arc two inches in diameter at 250 rpm.

This incubated vegetative medium (0.5 ml) is used to inoculate 50 ml of a production medium having the following composition:

| Ingredient | Amount (g/L.) |
|---|---|
| Glucose | 25.0 |
| Soybean grits | 20.0 |

-continued

| Ingredient | Amount (g/L.) |
| --- | --- |
| Molasses, blackstrap | 3.0 |
| Casein | 1.0 |
| CaCO$_3$ | 2.5 |
| Deionized water | q.s. 1 liter |

The inoculated production medium is incubated in a 250-ml Erlenmeyer flask at 30° C. for about two days on a shaker rotating through an arc two inches in diameter at 250 rpm.

B. Tank Fermentation of A-38533

In order to provide a larger volume of inoculum, 10 ml of incubated vegetative medium prepared as described above was used to inoculate 400 ml of a second-stage vegetative growth medium having the same composition as that of the vegetative medium (in duplicate). This second-stage medium was incubated in a 2-liter flask for about 24 hours at 30° C. on a shaker rotating through an arc 2 inches in diameter at 250 rpm.

Incubated second-stage vegetative medium (800 ml) thus prepared was used to inoculate 100 liters of sterile production medium having the same composition described in section A. The inoculated production medium was allowed to ferment in a 165-liter fermentation tank for about 1-2 days at a temperature of 30° C. The fermentation medium was aerated with sterile air at the rate of 0.25 V/V/M and was stirred with conventional agitators at 250 rpm.

EXAMPLE 2

Culture Preservation: Two ml of a 48-hr culture (vegetative media) are added to an osmotically balanced medium (2 ml) and maintained in the vapor phase of liquid nitrogen. The osmotically balanced medium has the following composition:

| Ingredient | Amount |
| --- | --- |
| Glycerol | 20% |
| Lactose | 10% |
| Water (deionized) | 70% |

The culture thus stored is thawed by placing the vial in a 43° C. water bath. A portion of the thawed solution (1 ml) is used to inoculate 50 ml of a vegetative medium having the same composition as that described in Example 1, Section A. The inoculated vegetative medium is used, as described in Example 1, either for shake-flask fermentation or to provide a larger inoculum for tank fermentation.

EXAMPLE 3

Separation of A-38533 antibiotic complex

Whole fermentation broth (200 liters), obtained as described in Example 2, was filtered using a filter aid (Hyflo Supercel, a diatomaceous earth, Johns-Manville Products Corp.) in a filter press. The filtered broth was chromatographed over a column containing 7 liters of polymeric adsorbent (Amberlite XAD-4, Rohm and Haas Co.), washing with water (35 L.) and water:methanol (3:1; 35 L.). The column was then eluted with water:methanol (1:1; 40 L.), collecting fractions having a volume of 4 liters. These fractions contained factor $A_1$ and smaller amounts of factors $A_2$ and B ($A_1$ major). The column was further eluted with water:methanol (1:4; 45 L.), again collecting fractions having a volume of 4 liters. These fractions contained factor B and smaller amounts of factors $A_1$, $A_2$ and C (B major). These two groups of combined fractions ($A_1$ major and B major) can be further combined to give the A-38533 complex.

EXAMPLE 4

Purification of the A-38533 Factors

After the initial purification over XAD-4 described in Example 3, the two groups of fractions ($A_1$ major and B major) were each treated in the following manner. The pH of the combined fractions was adjusted to pH 8.5 by the addition of sodium hydroxide. The resulting solution was evaporated under vacuum to remove the methanol, resulting in a volume of about 200 ml of aqueous solution. Methanol (200 ml) was added; the pH of this solution was adjusted to pH 3 by the addition of HCl. The resulting solution was precipitated by adding it to acetone (20 volumes). The precipitate which formed was separated by filtration, washed with acetone, and dried under vacuum. Using this procedure, the $A_1$ major precipitate gave from 42 to 127 grams of residue, and the B major precipitate gave from 30 to 175 grams of residue. In each case, the filtrates were dried under vacuum; the residues were each dissolved in methanol (250 ml); each methanol solution was added to diethyl ether (20 volumes) or to an acetone:dichloromethane (1:1) solution (20 volumes). The precipitates were again separated by filtration and dried to give additional amounts of from 10 to 56 grams of $A_1$ major fraction and from 30 to 75 grams of B major fraction.

Each of these preparations was further purified over Florisil (magnesium silicate, Floridin Co., P. O. Box 99, Tallahassee, Fla.; 10–200 mesh; 10 g material/liter Florisil). Each preparation was dissolved in methanol:water (2:1, 1 g/10 ml); the pH of each solution was adjusted to pH 8.5 by the addition of 5 N NaOH while stirring and warming for 15 minutes. Each resulting solution was absorbed onto Florisil (1 ml solution/2 ml Florisil) and placed in a vacuum oven at 40° C. to dry.

Alternatively, the combined XAD-4 fractions can be concentrated to a volume of approximately 200 ml; the pH of the concentrate adjusted to a pH of about 8.5 by the addition of NaOH; and the resulting solution dried directly on a two-fold excess of Florisil (400 ml) under vacuum. This sample can then be placed on a Florisil column (10–20 liters) and chromatographed as hereinafter described.

The Florisil column packing was washed with acetonitrile, decanting the fine particles and packing the remainder in the column. The column was washed with one column volume of acetonitrile:water (95:5) and reactivated with one column volume of acetonitrile. The Florisil load was placed atop the column and washed with five column volumes of acetonitrile (25 ml/min/liter Florisil). The column was eluted with five column volumes of acetonitrile:water (9:1) and then five column volumes of acetonitrile:water (85:15), collecting ¼-column-volume fractions. The active fractions were combined and concentrated to dryness under vacuum; the residue was redissolved in methanol. The methanol solution was added to 20 volumes of an acetone:dichloromethane (1:1) solution. The resulting precipitate was separated by filtration, washed with diethyl ether, and dried under vacuum. From 3 to 15 grams of purified $A_1$ major fraction and from 8 to 30 grams of B major fraction were obtained by this method.

Partial factor separation was achieved by chromatography on water-deactivated acetate-buffered silica gel 950 (60–200 mesh; 5 g material/liter silica gel). For this separation, each of the preparations was dissolved in methanol:water (2:1, 1 g/6 ml). The pH of this solution was adjusted to pH 8.5 by the addition of 5 N sodium hydroxide. The resulting solution was adsorbed onto Florisil (1 ml solution/2 ml Florisil) and dried in a vacuum oven at 40° C.

The silica gel for the column was washed sequentially with water (decanting and discarding the fine particles), 1 N sodium acetate, water, and acetonitrile:water (9:1) before packing into the column. The purified preparation adsorbed onto Florisil was placed atop the column; the column was then washed with five column volumes of acetonitrile:water (9:1).

In the case of the $A_1$ major preparations, elution was achieved with 10 column volumes of acetonitrile:water (7:1), collecting 1/5-column-volume fractions. The active fractions were analyzed by HPLC to determine factor content. Fractions were combined on the basis of factor content. Usually, two main fractions were collected. Each of these fractions was combined, concentrated to dryness, reconstituted in methanol, and precipitated into 20 volumes of acetone:dichloromethane (1:1). The precipitate was separated by filtration, washed with diethyl ether or acetone:dichloromethane (1:1) and then dried under vacuum. This separation gave from 3 to 6 grams of a mixture of factors $A_1$ and $A_2$ and from 0.5 to 2 grams of a mixture of factors $A_1$, $A_2$, and B.

For B major preparations, elution was achieved with 10 column volumes of acetonitrile:water (9:1), followed by seven column volumes of acetonitrile:water (7:1). Again, fractions were combined on the basis of HPLC data. Usually, two main fractions were collected and treated according to the procedure used for the $A_1$ major fractions to give from one to three grams of a mixture of factors B and C and from three to six grams of a mixture of factors $A_1$, $A_2$ and B.

Each of these purified preparations were then further purified over another Florisil column, packing the column as above described. The Florisil for the column was washed with acetonitrile, decanting and discarding fine particles. In each case the preparation (8 g of preparation/liter of Florisil) was placed atop the column, and the column was washed with five column volumes of acetonitrile:methanol (4:1). The column was eluted with 5 column volumes of acetonitrile:methanol (3:2) and then with 5 column volumes of acetonitrile:methanol (2:3). Active fractions were combined, concentrated to dryness, reconstituted in methanol, and precipitated into 20 volumes of acetone:dichloromethane (1:1). The precipitate was separated by filtration, washed with diethyl ether and dried under vacuum. The purified material recovered from these columns contained from 60 to 80% of the starting preparations.

Preparative HPLC was used for final factor separation. For preparative HPLC, a laboratory-synthesized reverse-phase packing designated LP-1/$C_{18}$ was used. A 550-ml column (1-in×120-cm; stainless steel) was packed as follows: the resin (LP-1/$C_{18}$) was suspended in carbon tetrachloride (5 ml/ml resin); the suspension was sonicated for twenty minutes. The suspension was then poured into the column, and a 3-liter reservoir was connected above the column. Carbon tetrachloride was pumped through the column until a constant pressure was achieved. The reservoir was removed, and cyclohexanol was pumped through the column at 5500 psi until proper packing was achieved as indicated by a symmetrical peak shape and a resolution of >2000 plates/meter. The separations were achieved using the following conditions:

| | |
|---|---|
| Flow rate | : 55 ml/min |
| Pressure | : 2100 psi |
| Solvent | : water:acetonitrile (varying from 10:1 to 5:1) plus 0.75 percent ammonium carbonate, pH 8.5 |
| Load | : 2–3 g |
| Detection | : by variable wavelength ultraviolet detector between 277 and 286 nanometers (10–20 nm higher than the maximum absorbance at 258 nm). |

A strip-chart recorder was used to trace the separation. Each of the peaks collected by HPLC was monitored for bioactivity as above described, was concentrated under vacuum to remove the methanol, and then was desalted over an XAD-4 column (about 1 g/200 ml XAD-4 resin). Each resin column was washed with 5 column volumes of water, 5 column volumes of water:methanol (3:1). For $A_1$ or $A_2$ preparations, the column was eluted with 5 column volumes of methanol:water (3:2); for B or C preparations, the column was eluted with 5 column volumes of methanol:water (4:1). After fractions were combined and concentrated to dryness, the residue was reconstituted in methanol and precipitated into 20 volumes of diethyl ether. The precipitate was separated by filtration, washed with diethyl ether, and dried. The following amounts of purified fractions were obtained in this manner:

Factor $A_1$—0.75–1.5 g
Factor $A_2$—0.1–0.3 g
Factor B—1.75–3 g
Factor C—0.1–0.3 g

EXAMPLE 5

Microbiological Assay for A-38533 Fermentation and Isolation Samples

Quantitative microbiological assays for A-38533 activity in fermentation and isolation samples were done by a paper-disc agar-diffusion method, using *Pseudomonas aeruginosa* ATCC 9027 as the indicator organism.

Seeded agar-diffusion plates were prepared by inoculating a nutrient agar medium with an appropriate concentration of the test culture, pouring 8 ml agar into each 20-×100-mm plastic petri dish.

The assay reference standard was A-38533 complex containing factors $A_1$, $A_2$, B, and C (with factor B the major component). This preparation was used on a unit basis. The activity of the highly purified factors is as follows:

$A_1$ 240–280 units/mg
$A_2$ 385–440 units/mg
B 130–175 units/mg
C 290–300 units/mg The standard dose-response curve was prepared to contain 100-50-25-12.5 units per ml. Phosphate buffer (0.1 M, pH 6.0) was used as diluent for the standard and samples. Incubation was at 37° for 18 hrs. Zones were read on a modified Fischer-Lilly Antibiotic Zone Reader.

We claim:

1. Antibiotic A-38533 factor $A_1$ which is a non-crystalline white powder having the following characteristics:
   (a) an approximate elemental composition of 53.3–54.9 percent carbon, 5.5–5.7 percent hydrogen, 12.4–12.7 percent nitrogen, 24.3–25.6 percent oxygen and 3.3–3.8 percent sulfur;
   (b) a molecular weight of about 840, as determined by mass spectrometry;
   (c) a molecular formula of $C_{37}H_{44}N_8O_{13}S$;
   (d) an infrared absorption spectrum in KBr pellet with significant absorption maxima at the following frequencies ($cm^{-1}$): 3363, 1665, 1593, 1552, 1518, 1465, 1396, 1363, 1268, 1185, 1112, 1073, 964, 887, 822, 792, 708, 635, 582, 555, and 490;
   (e) five titratable groups in 66 percent aqueous dimethylformamide with $pK_a$ values of approximately 5.93–6.02, 7.71–7.88, 10.80–10.90, 12.0–12.6, and greater than 13.0;
   (f) ultraviolet absorption spectra, in acidic or neutral methanol, with absorption maxima at 256 nm ($\epsilon$ 21,500) and 222 nm ($\epsilon$ 28,500) and, in basic methanol, absorption maxima at 290 nm ($\epsilon$ 7,500), 260 nm ($\epsilon$ 22,400), and 242 nm ($\epsilon$ 35,500);
   (g) is soluble in water, methanol, dimethyl sulfoxide, dimethylformamide, and in alcohol-water and tetrahydrofuran-water mixtures;
   (h) gives the following color reactions:

| | |
|---|---|
| Biuret | − |
| Folin | − |
| Anthrone | − |
| Dragendorff | − |
| Molish | + |
| Ehrlich | + |
| Sakaguchi | − |
| Ninhydrin | − |
| $FeCl_3$ | − |
| Pauly | + |

(i) contains (1) uracil and (2) hydroxyl and/or amino groups which are capable of acylation by standard procedures;
   (j) an $R_f$ value of approximately 0.55 on thin-layer chromatography using reverse-phase plates with fluorescent indicator (254 nm) and a 0.5 M citrate buffer (pH 4):methanol (1:1) solvent system;
   or the acid addition or cationic salt of A-38533 factor $A_1$.

2. Antibiotic A-38533 factor $A_2$ which is a non-crystalline white powder having the following characteristics:
   (a) an approximate elemental composition of 54.0–55.0 percent carbon, 5.0–6.0 percent hydrogen, 12.5–13.5 percent nitrogen, and 24.0–25.0 percent oxygen;
   (b) a molecular weight of about 822, as determined by mass spectrometry;
   (c) an infrared absorption spectrum in KBr pellet with significant absorption maxima at the following frequencies ($cm^{-1}$): 3350, 2940, 1656, 1535, 1505, 1458, 1383, 1255, 1170, 1100, 1062, 955, 880, 810, 775, 695, 625, 568, 543, 475, and 410;
   (d) ultraviolet absorption spectra, in acidic and neutral methanol, with absorption maxima at 256 nm ($\epsilon$ 20,500) and 222 nm ($\epsilon$ 26,500) and, in basic methanol, absorption maxima at 290 nm ($\epsilon$ 6400), 260 nm ($\epsilon$ 21,600), and 242 nm ($\epsilon$ 32,000);
   (e) is soluble in water, methanol, dimethyl sulfoxide, dimethylformamide, and in alcohol-water and tetrahydrofuran-water mixtures;
   (f) five titratable groups in 66 percent aqueous dimethylformamide with $pK_a$ values of approximately 6.10, 7.84, 10.80, <12.0 and <13.0;
   (g) contains hydroxyl and/or amino groups which are capable of acylation by standard procedures;
   (h) an $R_f$ value of approximately 0.49 on thin-layer chromatography using reverse-phase $C_{18}$ silylated silica gel with fluorescent indicator (254 nm) and a 0.5 M citrate buffer (pH 4):methanol (1:1) solvent system;
   or the acid addition or cationic salt of A-38533 factor $A_2$.

3. Antibiotic A-38533 factor B which is a non-crystalline white powder having the following characteristics:
   (a) an approximate elemental composition of 54.4–55.1 percent carbon, 5.3–5.6 percent hydrogen, 13.4–13.9 percent nitrogen, 22.1–22.9 percent oxygen and 3.3–3.6 percent sulfur;
   (b) a molecular weight of about 863, as determined by mass spectrometry;
   (c) a molecular formula of $C_{39}H_{45}N_9O_{12}S$;
   (d) an infrared absorption spectrum in KBr pellet with significant absorption maxima at the following frequencies ($cm^{-1}$): 3363, 1663, 1593, 1550, 1463, 1397, 1362, 1268, 1183, 1110, 1072, 965, 890, 820, 755, 708, 635, 580, and 555;
   (e) four titratable groups in 66% dimethylformamide with $pK_a$ values of approximately 6.20, 7.84, 10.80, and 12.75;
   (f) ultraviolet absorption spectra, in acidic and neutral methanol, with absorption maxima at 290 nm ($\epsilon$ 6150), 258 nm ($\epsilon$ 22,600), and 222 nm ($\epsilon$ 48,000), and, in basic methanol, absorption maxima at 290 nm ($\epsilon$ 8600), 260 nm ($\epsilon$ 23,000), 243 nm ($\epsilon$ 25,000) and 222 nm ($\epsilon$ 53,800);
   (g) is soluble in water, methanol, dimethyl sulfoxide, dimethylformamide, and in alcohol-water and tetrahydrofuran-water mixtures;
   (h) the following color reactions:

| | |
|---|---|
| Biuret | − |
| Folin | − |
| Anthrone | − |
| Dragendorff | − |
| Molish | + |
| Ehrlich | + |
| Sakaguchi | − |
| Ninhydrin | − |
| $FeCl_3$ | − |
| Pauly | + |

(i) contains the following component moieties: 2-amino-3-(methylamino)butyric acid, m-tyrosine, uracil and a dipeptide having the following structure:

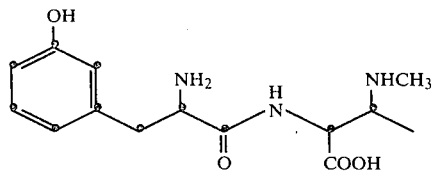

(j) contains hydroxyl and/or amino groups which are capable of acylation by standard procedures;

(k) an $R_f$ value of approximately 0.38 on thin-layer chromatography using reverse-phase $C_{18}$ silylated silica gel plates with fluorescent indicator (254 mm) and a 0.5 M citrate buffer (pH 4):methanol (1:1) solvent system; or the acid addition or cationic salt of A-38533 factor B.

4. Antibiotic A-38533 factor C which is a non-crystalline white powder having the following characteristics:
   (a) an approximate elemental composition of 54.5–54.7 percent carbon, 5.1–5.7 percent hydrogen, 13.8–14.1 percent nitrogen, and 22.2–23.9 percent oxygen;
   (b) a molecular formula of approximately 846, as determined by field-desorption mass spectrometry;
   (c) an infrared absorption spectrum in KBr pellet with significant absorption maxima at the following frequencies ($cm^{-1}$): 3362, 3040, 2950, 1660, 1540, 1455, 1385, 1260, 1175, 1098, 1063, 955, 875, 810, 745, 695, 570, 540, and 410;
   (d) four titratable groups in 66% aqueous dimethylformamide with $pK_a$ values of approximately 6.20, 7.86, 10.81, and 13.0;
   (e) ultraviolet absorption spectra, in acidic or neutral methanol, with absorption maxima at 290 nm ($\epsilon$ 6000), 259 nm ($\epsilon$ 21,000), and 222 nm ($\epsilon$ 46,000), and, in basic methanol, absorption maxima at 290 nm ($\epsilon$ 8500), 260 nm ($\epsilon$ 21,600), 243 nm ($\epsilon$ 25,400) and 222 nm ($\epsilon$ 51,700);
   (f) is soluble in water, methanol, dimethyl sulfoxide, dimethylformamide, and in alcohol-water and tetrahydrofuran-water mixtures;
   (g) the following color reactions:

| | |
|---|---|
| Biuret | − |
| Folin | − |
| Anthrone | − |
| Dragendorff | − |
| Molish | + |
| Ehrlich | + |
| Sakaguchi | − |
| Ninhydrin | − |
| $FeCl_3$ | − |
| Pauly | + |

(h) contains (1) uracil and (2) hydroxyl and/or amino groups which are capable of acylation by standard procedures;
   (i) an $R_f$ value of approximately 0.33 on thin-layer chromatography using reverse-phase $C_{18}$ silylated silica gel plates with fluorescent indicator (254 nm) and a 0.5 M citrate buffer (pH 4):methanol (1:1) solvent system; or the acid addition or cationic salt of A-38533 factor C.

5. The A-38533 antibiotic complex which is produced by cultivating *Streptomyces sp.* NRRL 11298 in a culture medium containing assimilable sources of carbon, nitrogen, and inorganic salts under submerged aerobic fermentation conditions until an optimal amount of antibiotic activity is produced.

6. The method of producing the A-38533 antibiotic complex which comprises cultivating *Streptomyces sp.* NRRL 11298 in a culture medium containing assimilable sources of carbon, nitrogen, and inorganic salts under submerged aerobic fermentation conditions until an optimal amount of antibiotic activity is produced.

7. The method of claim 6 which includes the additional step of isolating the A-38533 antibiotic complex from the culture medium.

8. The method of claim 7 which includes the additional step of isolating A-38533 factor $A_1$ from the separated A-38533 complex.

9. The method of claim 7 which includes the additional step of isolating A-38533 factor $A_2$ from the separated A-38533 complex.

10. The method of claim 7 which includes the additional step of isolating A-38533 factor B from the separated A-38533 complex.

11. The method of claim 7 which includes the additional step of isolating A-38533 factor C from the separated A-38533 complex.

* * * * *

UNITED STATES PATENT AND TRADEMARK OFFICE
CERTIFICATE OF CORRECTION

PATENT NO. : 4,180,564
DATED : December 25, 1979
INVENTOR(S) : Otis W. Godfrey, Ronald D. Johnson, and Ralph E. Kastner It is certified that error appears in the above–identified patent and that said Letters Patent are hereby corrected as shown below:

Column 6, line 57, "in" should read -- is --.

Column 15, line 45, after "reverse-phase" and before "plates with" add -- $C_{18}$ silylated silica gel --.

Column 16, line 6, "<12.0 and <13.0" should read -- >12.0 and >13.0 --.

*Signed and Sealed this*

*Twenty-fourth* Day of *February 1981*

[SEAL]

*Attest:*

*Attesting Officer*

RENE D. TEGTMEYER

*Acting Commissioner of Patents and Trademarks*